United States Patent
Machado et al.

(10) Patent No.: US 7,697,991 B2
(45) Date of Patent: Apr. 13, 2010

(54) METHODS OF TREATING NEUROLOGICAL CONDITIONS BY NEUROMODULATION OF INTERHEMISPHERIC FIBERS

(75) Inventors: Andre Machado, Sao Paulo SP (BR); Ali R. Rezai, Bratenhal, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 952 days.

(21) Appl. No.: 11/121,056

(22) Filed: May 4, 2005

(65) Prior Publication Data
US 2005/0283201 A1 Dec. 22, 2005

Related U.S. Application Data

(60) Provisional application No. 60/567,441, filed on May 4, 2004, provisional application No. 60/608,417, filed on Sep. 10, 2004, provisional application No. 60/608,418, filed on Sep. 10, 2004.

(51) Int. Cl.
*A61N 1/18* (2006.01)
(52) U.S. Cl. ...................................... 607/45
(58) Field of Classification Search ............. 607/45, 607/3
See application file for complete search history.

(56) References Cited

U.S. PATENT DOCUMENTS

| | | | |
|---|---|---|---|
| 5,711,316 A | 1/1998 | Elsberry et al. | |
| 5,938,688 A | 8/1999 | Schiff | |
| 6,058,331 A | 5/2000 | King | |
| 6,066,163 A | 5/2000 | John | |
| 6,128,537 A * | 10/2000 | Rise | 607/45 |
| 6,221,908 B1 | 4/2001 | Kilgard et al. | |
| 6,368,331 B1 | 4/2002 | Front et al. | |
| 6,466,822 B1 | 10/2002 | Pless | |
| 6,959,215 B2 * | 10/2005 | Gliner et al. | 607/45 |
| 6,990,377 B2 * | 1/2006 | Gliner et al. | 607/54 |
| 7,236,830 B2 * | 6/2007 | Gliner | 607/45 |
| 2002/0032375 A1 | 3/2002 | Bauch et al. | |
| 2002/0087201 A1 | 7/2002 | Firlik et al. | |
| 2002/0091419 A1 | 7/2002 | Firlik et al. | |
| 2002/0183607 A1 | 12/2002 | Bauch et al. | |

(Continued)

FOREIGN PATENT DOCUMENTS

WO WO 02/072194 A2 9/2002

(Continued)

OTHER PUBLICATIONS

International Search Report, International Application No. PCT/US05/15591, dated Nov. 9, 2006 (3 pgs.).

(Continued)

*Primary Examiner*—Carl H Layno
*Assistant Examiner*—Brian T Gedeon
(74) *Attorney, Agent, or Firm*—Kenyon & Kenyon LLP

(57) ABSTRACT

Methods of treating various medical conditions by neuromodulation of a target site of interhemispheric fibers. Such medical conditions include unilateral motor deficits, movement disorders, psychiatric disorders, speech or cognitive deficits associated with hemispheric lesions, visual deficits associated with hemispheric lesions, hereditary/genetic disorders, congenital malformations, infection disease, degenerative disorder, autoimmune disorders, and metabolic disorders. A method of providing recovery and rehabilitation from states of reduced consciousness by neuromodulating a target site of interhemispheric fibers is also provided.

24 Claims, 3 Drawing Sheets

U.S. PATENT DOCUMENTS

| | | |
|---|---|---|
| 2003/0097159 A1 | 5/2003 | Schiff et al. |
| 2003/0097161 A1 | 5/2003 | Firlik et al. |
| 2003/0125786 A1 | 7/2003 | Gliner et al. |
| 2003/0130706 A1 | 7/2003 | Sheffield et al. |
| 2004/0002635 A1 | 1/2004 | Hargrove et al. |
| 2004/0073270 A1 | 4/2004 | Firlik et al. |
| 2004/0088024 A1 | 5/2004 | Firlik et al. |
| 2005/0010261 A1* | 1/2005 | Luders et al. .......... 607/45 |
| 2005/0049649 A1 | 3/2005 | Luders et al. |

FOREIGN PATENT DOCUMENTS

| | | | |
|---|---|---|---|
| WO | WO 03/066157 | A2 | 8/2003 |

OTHER PUBLICATIONS

Machado et al., "Mapping of the Rat's Motor Area after Hemispherectomy: The Hemispheres as Potentially Independent Motor Brains,", Epilepsia, vol. 44, No. 4, pp. 500-506; 2003.

Marino, Jr. et al., "Functional Recovery after Combined Cerebral and Cerebella Hemispherectomy in the Rat," Stereotact Funct Neurosurg, 2001: 76:83-93.

Rhoton, A. L. Jr., MD., "The Lateral and Third Ventricles," Neurosurgery 51(4) Supplement 1:S1-207-271 (Oct. 2002).

Rhoton, A. L., Jr., MD, "The Cerebrum," Neurosurgery 51(4) Supplement 1:S1-1-52 (Oct. 2002).

* cited by examiner

METHODS OF TREATING NEUROLOGICAL CONDITIONS BY NEUROMODULATION OF INTERHEMISPHERIC FIBERS

CROSS-REFERENCE TO RELATED APPLICATIONS

The present application claims priority to U.S. Provisional Application Nos. 60/567,441 filed on May 4, 2004, 60/608/417 filed on Sep. 10, 2004 and 60/608,418 filed on Sep. 10, 2004, all of which are incorporated by reference herein.

FIELD OF THE INVENTION

The present invention relates to methods of treating neurological conditions by electrical and/or chemical neuromodulation of target site of interhemispheric fibers.

BACKGROUND OF THE INVENTION

Electrical stimulation of neural tissue is becoming an increasingly preferred form of therapy for various neurological conditions and disorders where existing therapies generate intolerable side effects, require repeated administration of treatment, or are simply ineffective in a subset of patients. Electrical stimulation provides distinct advantages over surgical lesioning techniques since electrical stimulation is a reversible and adjustable procedure that provides continuous benefits as the patient's disease progresses and the patient's symptoms evolve.

Currently, electrical stimulation of peripheral nerves and the spinal cord is approved for treatment of neuropathic pain. With respect to deep brain targets, electrical stimulation of the subthalamic nucleus and the globus pallidus interna is approved for treatment of Parkinson's disease and electrical stimulation of the ventral intermediate nucleus is approved for treatment of essential tremor.

There remains a need for further forms of neuromodulation to treat other disorders.

SUMMARY OF THE INVENTION

The present invention provides a method of treating neurological conditions resulting from a lesion of a cerebral hemisphere comprising placing a therapy delivery device in communication with a target site of interhemispheric fibers and activating the therapy delivery device to deliver a therapy signal to the target site to treat the neurological condition resulting from a lesion of a cerebral hemisphere. The present invention also provides a method of providing recovery and/or rehabilitation from a state of reduced consciousness.

DETAILED DESCRIPTION OF THE INVENTION

The present invention provides methods for treating neurological conditions resulting from a lesion of a cerebral hemisphere by neuromodulation of a target site of interhemispheric fibers.

Figure 1:
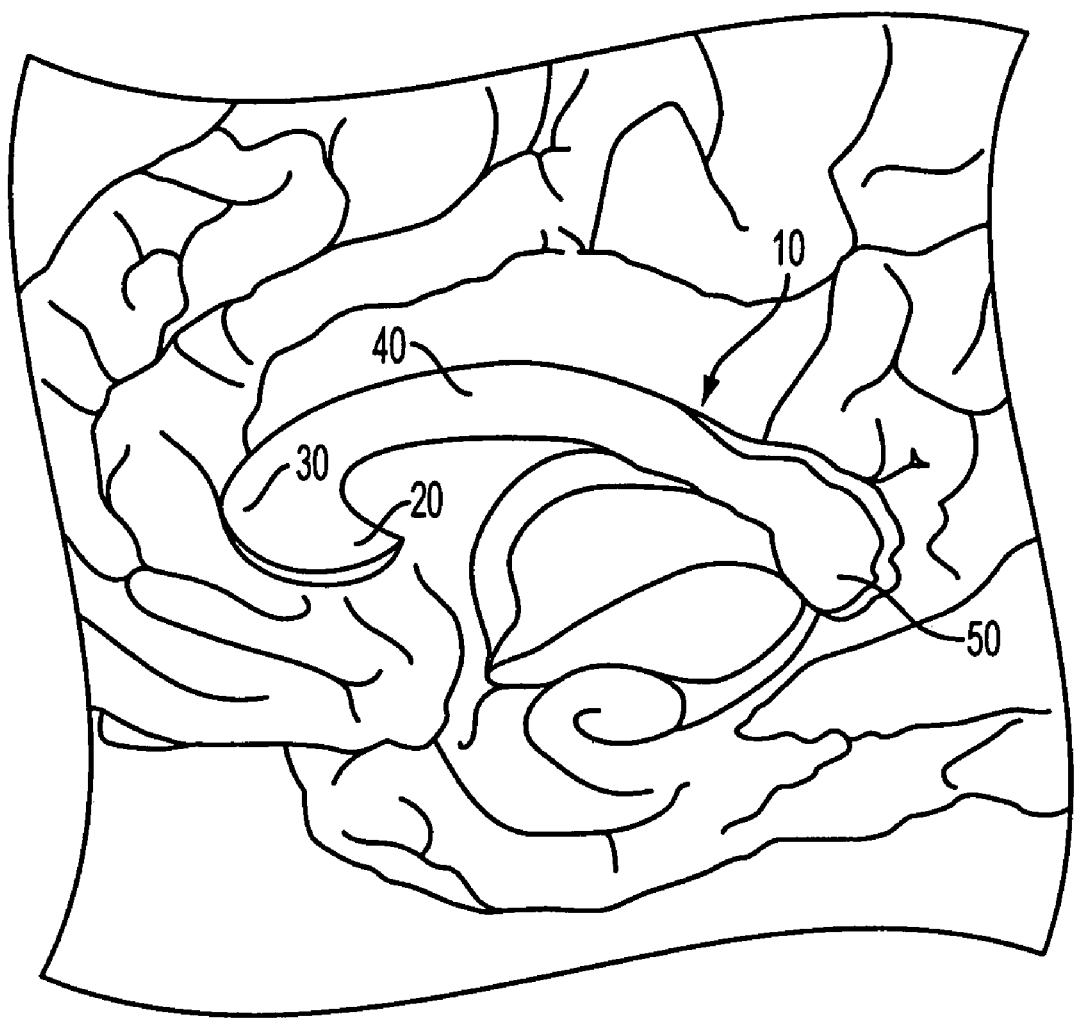
FIG. 1 is a schematic illustration of a corpus callosum.

Interhemispheric fibers are the fibers that provide communication between the left and right hemispheres. Interhemispheric fibers include the fibers that project from one hemisphere to another. The bundle of fibers is most dense in the midline, where it forms the corpus callosum. Referring to FIG. 1 and as is known to one of skill in the art, the corpus callosum 10 is located between the hemispheres in the floor of the interhemispheric fissure and the roof of the lateral ventricles. The corpus callosum 10 has two anterior parts, the rostrum 20 and the genu 30, a central part, the trunk 40 (also referred to as the body of the corpus callosum), and a posterior part, the splenium 50. The anterior parts 20 and 30 are situated in the midline deep to the upper part of the inferior frontal gyrus. As illustrated in FIG. 1, the genu 30 blends below into the rostrum 20, which is thin and tapered. Rostrum 20 is continuous downward in front of the anterior commissure, with the lamina terminalis. The curved genu 30 wraps around and forms the anterior wall and adjacent part of the roof of the frontal horn as it extends obliquely forward and lateral to connect the frontal lobes. As illustrated in FIG. 1, the genu 30 blends posteriorly into the trunk 40, located above the body of the lateral ventricle. The genu 30 and the trunk 40 of the corpus callosum 10 form the roof of both the frontal horn and the body of the lateral ventricle. The splenium 50 is situated deep to the supramarginal gyrus and the lower third of the pre-and postcentral gyri. As illustrated in FIG. 1, the splenium 50 is the thick rounded posterior end of the corpus callosum 10 and is situated dorsal to the pineal body and the upper part of the medial wall of the atrium. The splenium 50 contains a fiber tract, the forceps major, which forms a prominence, called the bulb, in the upper part of the medial wall of the atrium and occipital horn as it extends posteriorly to connect the occipital lobes. The cingulate gyrus surrounds and is separated from the corpus callosum 10 by the callosal sulcus. Further description of the corpus callosum 10 are described in Rhoton, Albert L. Jr. M.D. The Lateral and Third Ventricles. Neurosurgery 51(4) SUPPLEMENT 1: S1-207-271 (October 2002); Rhoton, Albert L. Jr. M.D. The Cerebrum. Neurosurgery. 51(4) SUPPLEMENT 1: S1-1-52 (October 2002), both of which are incorporated by reference herein.

Figure 2:
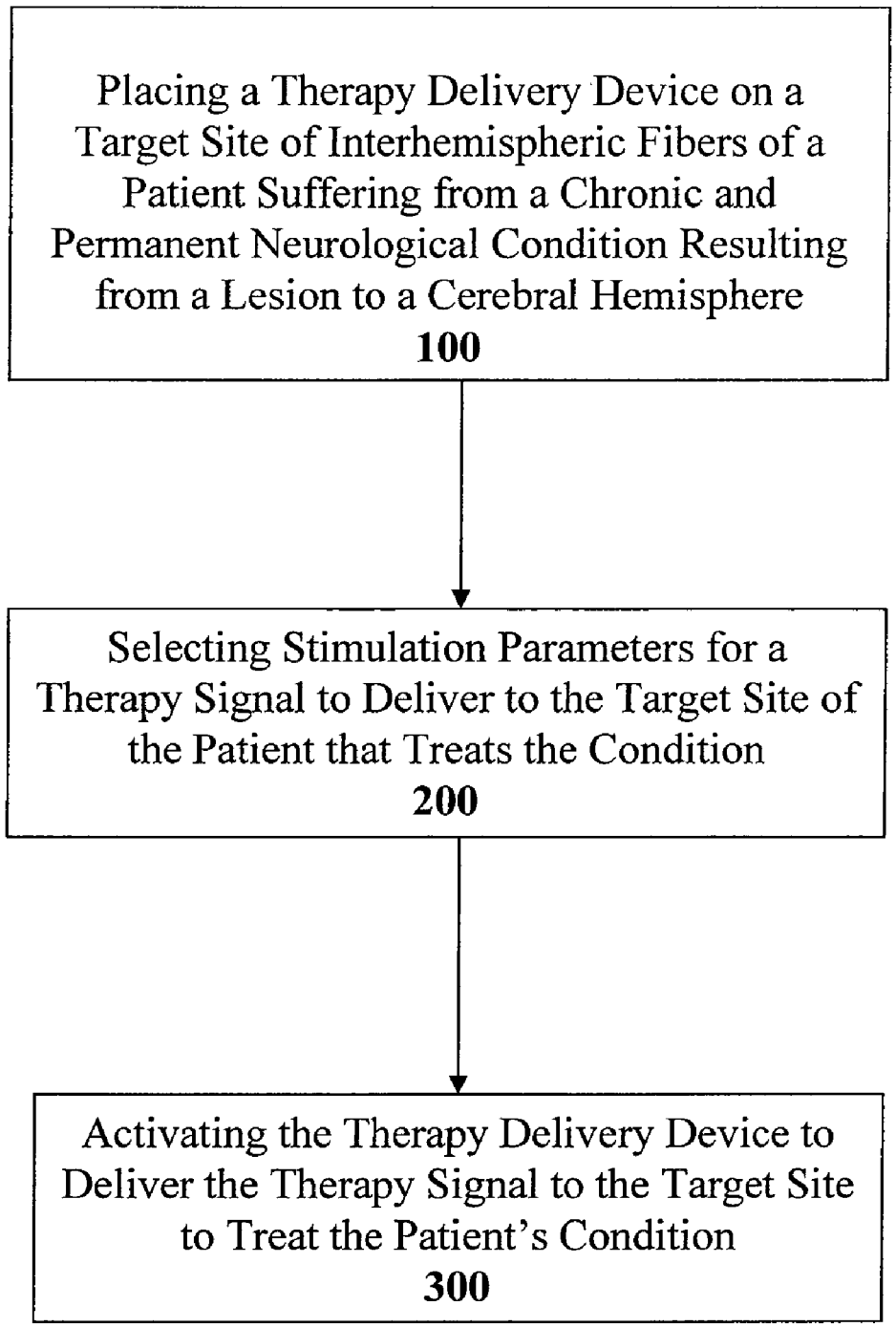
FIG. 2 is a flow chart depicting steps in a method of rehabilitating a patient who has had a chronic or permanent neurological condition resulting from a lesion to a cerebral hemisphere according to an embodiment of the present invention.

Referring to FIG. 2, an embodiment provides a method for rehabilitating a patient who has had a chronic and permanent neurological condition resulting from a lesion to a cerebral hemisphere comprising placing a therapy delivery device on a target site of interhemispheric fibers of the patient (100), selecting stimulation parameters for a therapy signal to deliver to the target site of the patient that treats the condition (200), and activating the therapy delivery device to deliver the therapy signal to the target site to treat the patient's condition (300).

Figure 3:
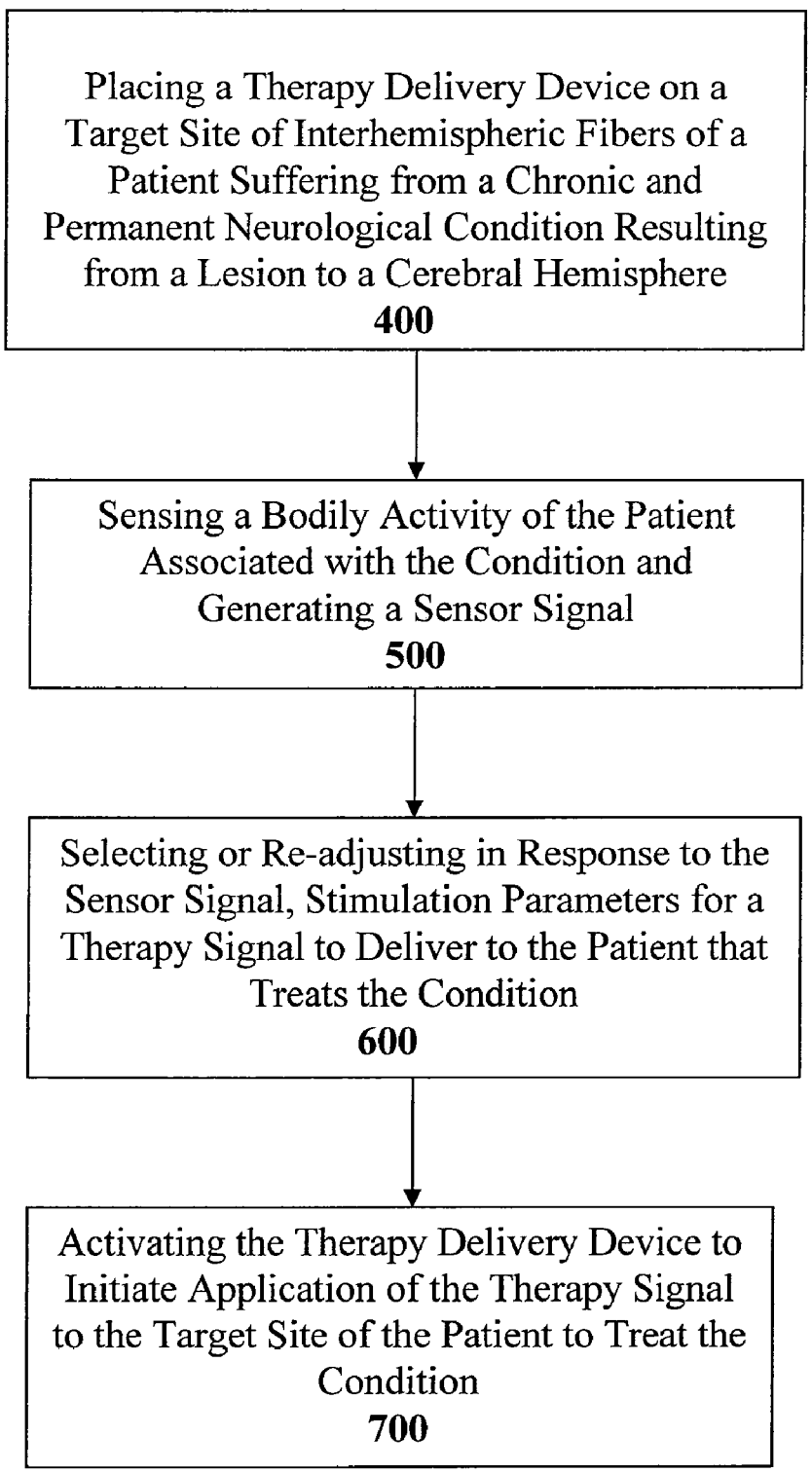
FIG. 3 is a flow chart depicting steps in a method of rehabilitating a patient who has had a chronic or permanent neurological condition resulting from a lesion to a cerebral hemisphere according to another embodiment of the present invention.

Referring to FIG. 3, another embodiment provides a method for rehabilitating a patient who has had a chronic and permanent neurological condition resulting from a lesion to a cerebral hemisphere comprising applying a therapy signal on a target site of interhemispheric fibers to the patient (400), sensing a bodily activity of the patient associated with the condition and generating a sensor signal (500), selecting or re-adjusting in response to the sensor signal, stimulation parameters for a therapy signal to deliver to the patient that treats the condition (600), and activating the therapy delivery device to initiate application of the therapy signal to the target site of the patient to treat the condition (700).

The methods of the present invention for treating neurological conditions encompass neuromodulation of any combination of one or more target sites of the interhemispheric fibers. As used herein, the term "treating" a neurological condition encompasses therapeutically regulating, preventing, improving, alleviating the symptoms of, reducing the effects of and/or diagnosing the neurological condition. As used herein, the term "neurological condition" encompasses any condition, disease, disorder, function, abnormality, or deficit that is caused by a lesion of a cerebral hemisphere. Although not wishing to be bound by theory, it is believed that neuromodulation of a target site encompassing the interhemispheric fibers modulates the communication between the cerebral hemispheres. Modulation of the interhemispheric communication may be used acutely, chronically, or even permanently in order to rehabilitate neurological function due to affections of a cerebral hemisphere.

Further, the methods of the present invention can be used to treat more than one neurological condition concurrently. Non-limiting examples of neurological conditions that can be treated according to the present invention include language deficits, visual deficits, motor deficits, cognitive deficits, learning deficits, sensory deficits, psychiatric disorders, movement disorders, pain syndromes, stroke, autism, consciousness, planning, or integration of function. Further, the neurological condition can be the result of any etiology including, for example, vascular, ischemic including stroke, thrombotic, embolic, infectious (including bacterial, viral, parasitic, fungal, abscessal), neoplastic, drug-induced, metabolic, immunological, inflammatory, collagenic, traumatic, surgical, chemotherapeutic, radiation, idiopathic, endocrinological, allergic, degenerative, congenital, or abnormal malformational causes.

Non-limiting examples of motor deficits that can be treated by the methods of the present invention include lack of coordination, gait disturbance, paralysis, hemiparesis, or paresis. Non-limiting examples of visual deficits include blindness. Non-limiting examples of cognitive deficits include aphasia and apraxia. A non-limiting example of a sensory deficit is hypoesthesia. Non-limiting examples of psychiatric disorders are addiction/substance abuse, obsessive compulsive disorder, generalized anxiety disorder, post traumatic stress disorder, panic attacks, social phobia, depression, bipolar disorder and other mood disorders, and schizophrenia. Non-limiting examples of movement disorders include Parkinson's disease, essential tremor, spasticity, rigidity, bradykinesia, post-traumatic movement disorder, post-ischemic and post-injury movement disorder. Non-limiting examples of pain syndromes include migraine headaches, including migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; reflex sympathetic dystrophy, cervicalgia; glossodynia, carotidynia; cricoidynia; otalgia due to middle ear lesion; gastric pain; sciatica; maxillary neuralgia; laryngeal pain, myalgia of neck muscles; trigeminal neuralgia; post-lumbar puncture headache; low cerebro-spinal fluid pressure headache; temporomandibular joint disorder; atypical facial pain; ciliary neuralgia; paratrigeminal neuralgia; petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia; carotidynia; Vidian neuralgia; and causalgia.

With respect to consciousness, the methods of the present invention can be used to provide recovery and/or rehabilitation from a state of reduced consciousness. Although the methods can be used to provide recovery and/or rehabilitation for any state of reduced consciousness, in preferred embodiments, the state of reduced consciousness is coma, a minimally conscious state, a persistent vegetative state, or torpor.

In an embodiment, the therapy delivery device is a stimulation lead and the therapy signal is an electrical signal. In such an embodiment, once the stimulation lead is placed in communication with the target site of the interhemispheric fibers, a pulse generator connected to the stimulation lead is activated thereby applying to the interhemispheric fibers an oscillating electrical signal having specified pulsing parameters. The oscillating electrical signal may be applied continuously or intermittently and the pulsing parameters, such as the pulse width, amplitude, frequency, voltage, current, intensity, and/or waveform may be adjusted to achieve affect a desired result. Specifically, the degree in which the interhemispheric fibers are stimulated to modulate the cortex on either hemisphere can be controlled by adjusting these parameters. Preferably, the oscillating electrical signal is operated at a voltage between about 20 to about 40-60V. More preferably, the oscillating electrical signal is operated at a voltage between about 1 V to about 15 V. Preferably, the electric signal is operated at a frequency range between about 2 Hz to about 2500 Hz. More preferably, the electric signal is operated at a frequency range between about 2 Hz to about 200 Hz. Preferably, the pulse width of the oscillating electrical signal is between about 10 microseconds to about 1,000 microseconds. More preferably, the pulse width of the oscillating electrical signal is between about 50 microseconds to about 500 microseconds. The waveform may be, for example, biphasic square wave, sine wave, or other electrically safe and feasible combination. Preferably, the application of the oscillating electrical signal is: monopolar when the stimulation lead is monopolar, bipolar when the stimulation lead is bipolar, and multipolar when the stimulation lead is multipolar. The stimulation lead may be placed in permanent or temporary communication with the target site to provide chronic or acute stimulation to the target site.

In another embodiment, the therapy delivery device is a drug port and the therapy signal is a chemical signal. The chemical signal can be delivered instead of or in addition to the electrical signal delivered by a stimulation lead according to the above-described embodiment. Specifically, a chemical agent may be delivered to a target site of the interhemispheric fibers prior to, concurrent with, subsequent to or instead of the electrical neuromodulation. The chemical agent may be a neurotransmitter mimick; neuropeptide; hormone; pro-hormone; antagonist, agonist, reuptake inhibitor, or degrading enzyme thereof; peptide; protein; therapeutic agent; amino acid; nucleic acid; stem cell or any combination thereof and may be delivered by a slow release matrix or drug pump. The chemical agents may be delivered continuously or intermittently.

Notwithstanding whether chemical and/or electrical neuromodulation is employed in the methods of the present invention, a closed-loop feedback mechanism may be employed in conjunction with such neuromodulation. In such an embodiment, a target site of the interhemispheric fibers is stimulated in response to a detected bodily activity associated with the neurological condition. In particular, this embodiment includes placing a therapy delivery device in communication with the target site of the interhemispheric fibers, detecting a bodily activity of the body associated with the neurological condition, and activating the therapy delivery device to apply a therapy signal to the target site in response to the detected bodily activity. Such bodily activity to be detected is any characteristic or function of the body, and includes, for example, respiratory function, body temperature regulation, blood pressure, metabolic activity, cerebral blood flow, pH levels, vital signs, galvanic skin responses, perspiration, electrocardiogram, electroencephalogram, action potential conduction, chemical production, body movement, response to external stimulation, speech, balance, motor activity, ocular activity, and cognitive function.

In another embodiment of the present invention, the bodily activity of the body includes an electrical or chemical activity of the body and may be detected by sensors located on or within the body. For example, such activity may be detected by sensors located within or proximal to the target site, distal to the target site but within the nervous system, or by sensors located distal to the target site outside the nervous system. Examples of electrical activity detected by sensors located within or proximal to the target site include sensors that measure neuronal electrical activity, such as the electrical activity characteristic of the signaling stages of neurons (i.e. synaptic potentials, trigger actions, action potentials, and neurotransmitter release) at the target site and by afferent and efferent pathways and sources that project to and from or communicate with the target site. For example, the sensors can measure, at any signaling stage, neuronal activity of any of the diffuse connections of the corpus callosum. In particular, the sensors may detect the rate and pattern of the neuronal electrical activity to determine the electrical signal to be provided to the stimulation lead.

Examples of chemical activity detected by sensors located within or proximal to the target site include sensors that measure neuronal activity, such as the modulation of neurotransmitters, hormones, pro-hormones, neuropeptides, peptides, proteins, electrolytes, or small molecules by the target site and modulation of these substances by afferent and efferent pathways and sources that project to and from the corpus callosum or communicate with the corpus callosum.

With respect to detecting electrical or chemical activity of the body by sensors located distal to the target site but still within the nervous system, such sensors could be placed in the brain, the spinal cord, cranial nerves, and/or spinal nerves. Sensors placed in the brain are preferably placed in a layer-wise manner in the direction of increasing proximity to the interhemispheric fibers. For example, a sensor could be placed on the scalp (i.e. electroencephalogram), in the subgaleal layer, on the skull, in the dura mater, in the sub dural layer and in the parenchyma (i.e. in the frontal lobe, occipital lobe, parietal lobe, temporal lobe) to achieve increasing specificity of electrical and chemical activity detection. The sensors could measure the same types of chemical and electrical activity as the sensors placed within or proximal to the target site as described above.

With respect to detecting electrical or chemical activity by sensors located distal to the target site outside the nervous system, such sensors may be placed in venous structures and various organs or tissues of other body systems, such as the endocrine system, muscular system, respiratory system, circulatory system, urinary system, integumentary system, and digestive system or such sensors may detect signals from these various body systems. All the above-mentioned sensing systems may be employed together or any combination of less than all sensors may be employed together.

After the sensor(s) detect the relevant bodily activity associated with the neurological condition, the sensors generate a sensor signal. The sensor signal is processed by a sensor signal processor and provides a control signal to the stimulation controller, which is a signal generator or drug pump depending on whether electrical or chemical neuromodulation is desired. The stimulation controller, in turn, generates a response to the control signal by activating the therapy delivery device. The therapy delivery device then applies a therapy signal to the target site of the interhemispheric fibers to treat the neurological condition. In the case of electrical neuromodulation, the control signal may be an indication to initiate, terminate, increase, decrease or change the rate or pattern of a pulsing parameter of the electrical stimulation and the therapy signal can be the respective initiation, termination, increase, decrease or change in rate or pattern of the respective pulsing parameter. In the case of chemical neuromodulation, the control signal can be an indication to initiate, terminate, increase, decrease or change the rate or pattern of the amount or type of chemical agent administered, and the therapy signal can be the respective initiation, termination, increase, decrease or change in the rate or pattern of the amount or type of chemical agent administered. The processing of closed-loop feedback systems for electrical and chemical stimulation are described in more detail in respective U.S. Pat. Nos. 6,058,331 and 5,711,316, both of which are incorporated by reference herein.

Although the application of sensors to detect bodily activity are within the scope and spirit of the present invention, the present invention also contemplates the relevant bodily activity to be detected without sensors. In such case the neuromodulation parameters are adjusted manually in response to the clinical course of the neurological condition or to reporting by the patient.

Although not wishing to be bound by the description of a particular procedure, one exemplary procedure effectuating the methods of the present invention shall now be described with respect to electrical neuromodulation of the corpus callosum. Generally, the procedure begins with the patient having a stereotactic head frame mounted to the patient's skull, although frameless techniques may also be used. The patient then typically undergoes a series of MRI and/or CT sessions, during which a series of two dimensional slice images of the patient's brain are built up into a quasi-three dimensional map in virtual space. This map is then correlated to the three dimensional stereotactic frame of reference in the actual surgical field. In order to align these two coordinate frames, both the instruments and the patient should be situated in correspondence to the virtual map. A current method of achieving this alignment is to rigidly mount to the head frame to the surgical table. Subsequently, a series of reference points are established relative to aspects of the frame and patient's skull, so that a computer can adjust and calculate the correlation between the actual surgical field of the patient's head and the virtual space model of the patient's brain MRI scans. Initial anatomical localization of the corpus callosum is usually achieved using the MRI images.

Another method of localizing the corpus callosum involves the fusion of functional and structural medical imaging. Such methods for localizing targets in the body and guiding diagnostic or therapeutic instruments toward a target region in the body have been described in U.S. Pat. No. 6,368,331, issued on Apr. 9, 2002 to Front et al., U.S. Patent Application Publication No. U.S. 2002/0032375, published Mar. 14, 2002 by Bauch et al., and U.S. Patent Application Publication No. U.S. 2002/0183607, published Dec. 5, 2002 by Bauch et al., all of which are hereby incorporated by reference in their entireties. Methods for target localization specifically within the nervous system, including the brain, have been described in U.S. Provisional Application No. 60/353,695, filed Feb. 1, 2002, by Rezai et al. which is hereby incorporated by reference in its entirety. Specifically, provided in U.S. Provisional Application No. 60/353,695 is a method of medical imaging, comprising: placing a fiducial marker proximate to an area of a body to be imaged; obtaining a first image of the area of the body using a first medical imaging technique, the first image including a first image of the fiducial marker; obtaining a second image of the area of the body using a second medical imaging technique, the second image including a second image of the fiducial marker, the second medical imaging technique being different than the first medical imaging technique; superimposing the first image of the area of the body and the second image of the area of the body; and aligning the first image of the first fiducial marker with the second image of the fiducial marker. Useful medical imaging techniques to obtain functional images include but are not limited to functional MRI, PET or MEG. Useful medical imaging techniques to obtain structural images include but are not limited to volumetric MRI and CT.

Subsequent to the stereotactic imaging (or functional and structural imaging), acquisition of the images, and anatomical localization, the patient is taken to the operating room. A patient is positioned on the operating table in the supine position under general endotracheal anesthesia. The patient's head is immobilized using a pin head holder. An incision is made on skin of the skull, in one of several fashions: frontotemporal, bifrontal, frontal, frontotemporoparietal or other. After the skip flap is retracted, a frontal-parietal craniotomy is performed passing the midline to expose the superior sagital sinus. Alternatively, other craniotomies can also be made, such as a bifrontal craniotomy, frontotemporo craniotomy, frontotemporoparietal craniotomy, craniotomies extended to the controlateral side and other variations. The dura mater is tacked to the skull and opened in an arc with the dura mater's base toward the midline. Dissection is continued until the interhemispheric fissure is adequately exposed at the level of the falx. The interhemispheric fissure is dissected using microneurosurgical techniques known to one of skill in the art. The interhemispheric fissure is dissected until the corpus callosum is adequately exposed. The branches of the anterior communicating artery may be dissected away to create necessary area to implant the stimulation lead.

The stimulation lead can be delivered and placed on the top surface of corpus callosum, in the thickness corpus callosum, or on the bottom surface of the corpus callosum, by any appropriate method known in the art. For example, an installation tool may be used which grips and folds a lead having electrodes disposed thereon and then delivers and places the lead on the corpus callosum.

The stimulation lead may also be delivered to the corpus callosum via a cannula. In such a case, the lead is folded and inserted into the cannula and delivered to the corpus callosum. As the lead exits the distal end of cannula, the lead unfolds and can assume the operative position on the corpus callosum.

Of course, other methods of delivering and implanting a stimulation lead, including using conventional neurosurgical instrumentation, are within the knowledge of one of skill in the art. For example, the stimulation lead can be delivered by any minimally invasive technique such as endoscopically and/or intravascularly. Specifically, the stimulation lead can be delivered to the corpus callosum neuroendoscopically through the lateral ventricle such that stimulation lead is in contact with the bottom surface of the corpus callosum. Other details regarding the delivery of a stimulation lead to the corpus callosum as well as a preferred stimulation lead are described in co-pending U.S. Provisional Application No. 60/608,417 entitled "Corpus Callosum Neuromodulation Assembly" filed on Sep. 10, 2004.

Once the stimulation lead is placed on the corpus callosum, the stimulation lead can be anchored in the brain by securing the stimulation lead to the dura mater of the falx and/or the dura mater of the convexity, for example. Closure of the craniotomy can be performed using standard methods well-known to one of skill in the art. In the case of an implantable stimulation assembly, a tunneling device may then be used to dissect a subcutaneous tunnel down to the subclavicular level, where a subcutaneous pocket can be made to accommodate an implantable pulse generator. An extension wire can then be passed through the tunnel to connect the neuromodulation assembly to the pulse generator. Alternatively, other sites can be used for implantation of the pulse generator, such as the abdominal wall and the lower back area below the posterior iliac crest.

The above-described procedure is only exemplary and the methods of the present invention are in no way limited to any particular procedure. Further, the foregoing description has been set forth merely to illustrate the invention and are not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. For example, although methods of treating specific medical conditions are described, the interhemispheric fibers can be stimulated to treat medical conditions related to the skeletal system, the immunological system, the vascular/hematological system, the muscular/connective tissue system, the neurological system, the visual system, the auditory and vestibular system, the dermatological system, the endocrine system, the olfactory system, the cardiovascular system, the genitourinary system, the gastrointestinal system, the respiratory system, as well as treating mass lesions such as abscesses, tumors, and aneurysms. Furthermore, all references cited herein are incorporated by reference in their entirety.

We claim:

1. A method for rehabilitating a patient comprising:
identifying a patient having a chronic and permanent neurological condition resulting from a lesion to a cerebral hemisphere;
placing a therapy delivery device on a target site of interhemispheric fibers of the patient;
selecting stimulation parameters for a therapy signal; and
activating the therapy delivery device to deliver the therapy signal to the target site to treat the patient's condition.

2. The method of claim 1, wherein the neurological condition is at least one of a language deficit, a visual deficit, a motor deficit, a cognitive deficit, a learning deficit, and a sensory deficit.

3. The method of claim 2, wherein the motor deficit is at least one of lack of coordination, paralysis, hemiparesis, and paresis.

4. The method of claim 2, wherein the visual deficit is blindness.

5. The method of claim 2, wherein the cognitive deficit is apraxia.

6. The method of claim 2, wherein the sensory deficit is hypoesthesia.

7. The method of claim 2, wherein the language deficit is aphasia.

8. The method of claim 1, wherein the neurological condition is at least one of a psychiatric disorder and a movement disorder.

9. The method of claim 8, wherein the psychiatric disorder is at least one of depression and schizophrenia.

10. The method of claim 8, wherein the movement disorder is at least one of tremor and spasticity.

11. The method of claim 1, wherein the neurological condition is a pain syndrome.

12. The method of claim 11, wherein the pain syndrome is at least one of chronic pain, neuropathic pain, complex regional pain syndrome I and II, headache, and atypical facial pain.

13. The method of claim 12, wherein the headache is at least one of a migraine headache or a cluster headache.

14. The method of claim 12, wherein the neuropathic pain is at least one of chronic neuropathic pain and neuropathic facial pain.

15. The method of claim 1, wherein the neurological condition is stroke.

16. The method of claim 1, wherein the neurological condition is autism.

17. The method of claim 1, wherein the neurological condition is at least one of a state of reduced consciousness and a minimally conscious state.

18. The method of claim 1, wherein the neurological condition is a deficit in planning function.

19. The method of claim 1, wherein the neurological condition is a deficit in integration of function.

20. The method of claim 1, wherein the target site is the corpus callosum.

21. The method of claim 1, wherein the therapy signal comprises at least one of an electrical signal, a chemical signal or both the electrical signal and the chemical signal.

22. The method of claim 1, wherein the therapy signal is a chemical signal.

23. The method of claim 1, wherein the therapy signal is both an electrical signal and a chemical signal.

24. A method for rehabilitating a patient comprising:
  identifying a patient having a chronic and permanent neurological condition resulting from a lesion to a cerebral hemisphere;
  placing a therapy delivery device on a target site of interhemispheric fibers of the patient;
  sensing a bodily activity of the patient associated with the condition and generating a sensor signal;
  in response to the sensor signal, selecting or re-adjusting stimulation parameters for a therapy signal; and
  activating the therapy delivery device to initiate application of the therapy signal to the target site of the patient to treat the condition.

* * * * *